(12) United States Patent
Hayashi et al.

(10) Patent No.: US 7,438,416 B2
(45) Date of Patent: Oct. 21, 2008

(54) OPTOMETRIC APPARATUS

(75) Inventors: Akihiro Hayashi, Toyokawa (JP); Yoshinobu Hosoi, Gamagori (JP); Hidetaka Hoshino, Nukata-gun (JP)

(73) Assignee: Nidek Co., Ltd (JP)

( * ) Notice: Subject to any disclaimer, the term of this patent is extended or adjusted under 35 U.S.C. 154(b) by 590 days.

(21) Appl. No.: 10/834,982

(22) Filed: Apr. 30, 2004

(65) Prior Publication Data

US 2004/0218147 A1 Nov. 4, 2004

(30) Foreign Application Priority Data

May 2, 2003 (JP) ............................. 2003-127482

(51) Int. Cl.
*A61B 3/02* (2006.01)
(52) U.S. Cl. .................. 351/235; 351/229; 351/233; 351/234
(58) Field of Classification Search .................. 351/235
See application file for complete search history.

(56) References Cited

U.S. PATENT DOCUMENTS

| | | | |
|---|---|---|---|
| 3,791,719 A * | 2/1974 | Kratzer et al. ............... 351/211 |
| 3,969,020 A | 7/1976 | Lynn et al. |
| 4,105,303 A | 8/1978 | Guyton |
| 4,697,598 A | 10/1987 | Bernard et al. |
| 4,798,457 A | 1/1989 | Morohashi et al. |
| 4,943,162 A | 7/1990 | Sims |
| 5,463,430 A | 10/1995 | Isogai et al. |
| 5,812,241 A | 9/1998 | Doms et al. |
| 6,046,861 A | 4/2000 | Steele |
| 6,048,064 A * | 4/2000 | Hosoi et al. ................. 351/212 |
| 2001/0024263 A1 | 9/2001 | Naniyo |
| 2003/0030774 A1 | 2/2003 | Raasch |
| 2003/0081175 A1 | 5/2003 | Hosoi |

FOREIGN PATENT DOCUMENTS

| | | |
|---|---|---|
| JP | 05-176893 | 7/1993 |
| JP | 10-028675 A | 2/1998 |
| JP | 11-267100 | 10/1999 |
| JP | 2000-5131 | 11/2000 |

OTHER PUBLICATIONS

Result of Consultation, App. No. 04 010 335.0-1265, Ref. 56NI1341, Oct. 17, 2007 (11 pages).
Japanese Office Action dated Jan. 24, 2007 for corresponding Japanese Application No. 2003-127482.

* cited by examiner

*Primary Examiner*—Jessica T Stultz
(74) *Attorney, Agent, or Firm*—Rader Fishman & Grauer PLLC; Ronald P. Kananen (57) ABSTRACT

An optometric apparatus for examining refractive power of an examinee's eye subjectively, capable of performing highly-precise examination. The apparatus has a test window through which a presented optotype is seen, a first spherical-power applying unit which applies spherical power to the eye by changing a combination of spherical lenses in the window, a cylindrical-power applying unit which applies cylindrical power to the eye by changing a relative angle of a cylindrical axis of cylindrical lenses in the window, a second spherical-power applying unit including a spherical lens for correction, an instruction unit which instructs examination spherical and cylindrical power, a power-determining unit which determines power applied by the power-applying units so that a difference between the instructed examination power, and resultant spherical and cylindrical power through conversion for a spectacles wearing reference position falls within a predetermined permissible difference, and a control unit which controls driving of the power-applying units.

2 Claims, 9 Drawing Sheets

|           | 1 | 2     | 3      | 4              | 5              | 6     |
|-----------|---|-------|--------|----------------|----------------|-------|
| Strong SPH| 0 | -9.00 | -18.00 | BL             | +18.00         | +9.00 |
| Middle SPH| 0 | -1.50 | -3.00  | -4.50          | +3.00          | +1.50 |
| Weak SPH  | 0 | -0.25 | -0.50  | -0.75          | +0.50          | +0.25 |
| CYL       | Stokes' cross cylinder ||||||
| AUX1      | 0 | S-0.12| PH     | Right 6Δ/Left 10Δ | Right R/Left G | Pola  |
| AUX2      | 0 | RP    | MR     | ±0.5XC         | ±0.25AXC       | PD    |

|  | 1 | 2 | 3 | 4 | 5 | 6 |
|---|---|---|---|---|---|---|
| Strong SPH | 0 | -9.00 | -18.00 | BL | +18.00 | +9.00 |
| Middle SPH | 0 | -1.50 | -3.00 | -4.50 | +3.00 | +1.50 |
| Weak SPH | 0 | -0.25 | -0.50 | -0.75 | +0.50 | +0.25 |
| Strong CYL | 0 | -1.50 | -3.00 | -4.50 | -6.00 | -7.50 |
| Weak CYL | 0 | -0.25 | -0.50 | -0.75 | -1.00 | -1.25 |

FIG. 5

When examination spherical power S = -5.25 D    Unit = D

| Examination cylindrical power C | L 4 | L 5 | Resultant cylindrical power through conversion for reference position C | Difference | Permissible difference |
|---|---|---|---|---|---|
| -0.25 | 0.00 | -0.25 | -0.24 | 0.01 | Within ±0.06 |
| -0.50 | 0.00 | -0.50 | -0.48 | 0.02 | |
| -0.75 | 0.00 | -0.75 | -0.71 | 0.04 | |
| -1.00 | 0.00 | -1.00 | -0.95 | 0.05 | |
| -1.25 | 0.00 | -1.25 | -1.19 | 0.06 | |
| -1.50 | -1.50 | 0.00 | -1.43 | 0.07 | |
| -1.75 | -1.50 | -0.25 | -1.66 | 0.09 | |
| -2.00 | -1.50 | -0.50 | -1.89 | 0.11 | |
| -2.25 | -1.50 | -0.75 | -2.12 | 0.13 | |
| -2.50 | -1.50 | -1.00 | -2.35 | 0.15 | |
| -2.75 | -1.50 | -1.25 | -2.58 | 0.17 | |
| -3.00 | -3.00 | 0.00 | -2.86 | 0.14 | |
| -3.25 | -3.00 | -0.25 | -3.08 | 0.17 | Within ±0.09 |
| -3.50 | -3.00 | -0.50 | -3.30 | 0.20 | |
| -3.75 | -3.00 | -0.75 | -3.52 | 0.23 | |
| -4.00 | -3.00 | -1.00 | -3.75 | 0.25 | |
| -4.25 | -3.00 | -1.25 | -3.97 | 0.28 | |
| -4.50 | -4.50 | 0.00 | -4.29 | 0.21 | |
| -4.75 | -4.50 | -0.25 | -4.50 | 0.25 | |

FIG. 6

Permissible difference in spherical refractive power

| Spherical refractive power (Absolute value) D | Permissible difference (D) |
|---|---|
| 3.00 or less | ± 0.06 |
| 3.00 excl. to 6.00 incl. | ± 0.09 |
| 6.00 excl. to 9.00 incl. | ± 0.12 |
| 9.00 excl. to 12.00 incl. | ± 0.15 |
| 12.00 excl. to 15.00 incl. | ± 0.18 |
| above 15.00 | ± 0.25 |

FIG. 7 A

Permissible difference in cylindrical (astigmatic) refractive power

| Refractive power in steepest meridian (Absolute value) D | Cylindrical refractive power (Absolute value) D | | | | |
|---|---|---|---|---|---|
| | 0.50 or less | 0.50 excl. to 1.00 incl. | 1.00 excl. to 3.00 incl. | 3.00 excl. to 6.00 incl. | above 6.00 |
| | Permissible difference (D) | | | | |
| 5.00 or less | 0.06 | 0.06 | 0.06 | 0.09 | 0.12 |
| 5.00 excl. to 10.00 incl. | 0.06 | 0.06 | 0.06 | 0.09 | 0.12 |
| 10.00 excl. to 15.00 incl. | 0.06 | 0.06 | 0.09 | 0.12 | 0.18 |
| above 15.00 | 0.06 | 0.09 | 0.12 | 0.18 | 0.25 |

Examination cylindrical power C=-4.25D (ε=50.00°) →Spherical power to be corrected S-2.12D

| Examination spherical power S | L1 | L2 | L3 | L5 | S in total | ε=50° Resultant cylindrical power through conversion for reference position C | ε=50° Resultant spherical power through conversion for reference position S | Correction ε | ε correction Generated cylindrical power C | Resultant cylindrical power through conversion for reference position after ε correction C | Resultant spherical power through conversion for reference position after ε correction S |
|---|---|---|---|---|---|---|---|---|---|---|---|
| 0.00 | 0.00 | -1.50 | -0.50 | -0.12 | -2.12 | -4.13 | -0.04 | 50.75° | -4.35 | -4.25 | 0.01 |
| -1.00 | 0.00 | -3.00 | 0.00 | -0.12 | -3.12 | -4.14 | -1.05 | 50.90° | -4.37 | -4.25 | -0.99 |
| -3.00 | 0.00 | -4.50 | -0.50 | -0.12 | -5.12 | -4.06 | -3.07 | 51.60° | -4.45 | -4.25 | -2.97 |
| -5.25 | -9.00 | 1.50 | 0.25 | -0.12 | -7.37 | -4.31 | -5.21 | 49.50° | -4.19 | -4.25 | -5.25 |
| -6.00 | -9.00 | 1.50 | -0.50 | -0.12 | -8.12 | -4.26 | -6.00 | none | | | |
| -9.50 | -9.00 | -3.00 | 0.50 | -0.12 | -11.62 | -4.17 | -9.54 | 50.60° | -4.33 | -4.25 | -9.51 |
| 6.00 | 9.00 | -4.50 | -0.50 | -0.12 | 3.88 | -4.06 | 5.93 | 51.60° | -4.45 | -4.25 | 6.03 |

→Allowable without correction ε

FIG. 8B

Examination cylindrical power C=-3.00D (ε=40.00°) →Spherical power to be corrected S-1.50D

| Examination spherical power S | L1 | L2 | L3 | L5 | S in total | ε=50° Resultant cylindrical power through conversion for reference position C | ε=50° Resultant spherical power through conversion for reference position S | Correction ε | ε correction Generated cylindrical power C | Resultant cylindrical power through conversion for reference position after ε correction C | Resultant spherical power through conversion for reference position after ε correction S |
|---|---|---|---|---|---|---|---|---|---|---|---|
| 0.00 | 0.00 | -1.50 | 0.00 | 0.00 | -1.50 | -2.96 | -0.02 | none | | | |
| -1.00 | 0.00 | -1.50 | -1.00 | 0.00 | -2.50 | -2.91 | -1.03 | 40.70° | -3.08 | -3.00 | -0.99 |
| -3.00 | 0.00 | -4.50 | 0.00 | 0.00 | -4.50 | -2.89 | -3.06 | 40.90° | -3.11 | -3.00 | -3.00 |
| -5.25 | -9.00 | 3.00 | -0.75 | 0.00 | -6.75 | -3.03 | -5.25 | none | | | |
| -11.00 | -9.00 | -3.00 | -0.50 | 0.00 | -12.50 | -2.90 | -11.04 | 40.80° | -3.10 | -3.00 | -10.99 |
| 4.00 | 0.00 | 3.00 | 0.50 | 0.00 | 3.50 | -3.09 | 5.06 | 39.30° | 2.91 | -3.00 | 5.01 |
| 6.00 | 9.00 | -4.50 | 0.00 | 0.00 | 4.50 | -2.89 | 5.94 | 40.90° | 3.11 | -3.00 | 6.00 |

FIG. 9

When examination spherical power S = −5.25 D  Unit = D

| Examination cylindrical power C | L4 | L5 | Resultant cylindrical power through conversion for reference position C | Cylindrical lens for correction | Difference | Permissible difference |
|---|---|---|---|---|---|---|
| −0.25 | 0.00 | −0.25 | −0.24 |  | 0.01 | Within ±0.06 |
| −0.50 | 0.00 | −0.50 | −0.48 |  | 0.02 | |
| −0.75 | 0.00 | −0.75 | −0.71 |  | 0.04 | |
| −1.00 | 0.00 | −1.00 | −0.95 |  | 0.05 | |
| −1.25 | 0.00 | −1.25 | −1.19 |  | 0.06 | |
| −1.50 | −1.50 | 0.00 | −1.43 | −0.12 | −0.05 | |
| −1.75 | −1.50 | −0.25 | −1.66 | −0.12 | −0.03 | |
| −2.00 | −1.50 | −0.50 | −1.89 | −0.12 | −0.01 | |
| −2.25 | −1.50 | −0.75 | −2.12 | −0.12 | 0.01 | |
| −2.50 | −1.50 | −1.00 | −2.35 | −0.12 | 0.03 | |
| −2.75 | −1.50 | −1.25 | −2.58 | −0.12 | 0.05 | |
| −3.00 | −3.00 | 0.00 | −2.86 | −0.12 | 0.02 | |
| −3.25 | −3.00 | −0.50 | −3.30 |  | −0.05 | Within ±0.09 |
| −3.50 | −3.00 | −0.75 | −3.52 |  | −0.02 | |
| −3.75 | −3.00 | −1.00 | −3.75 |  | 0.00 | |
| −4.00 | −3.00 | −1.25 | −3.97 |  | 0.03 | |
| −4.25 | −4.50 | 0.00 | −4.29 |  | −0.04 | |
| −4.50 | −4.50 | −0.25 | −4.50 |  | 0.00 | |
| −4.75 | −4.50 | −0.50 | −4.72 |  | 0.03 | |
| −5.00 | −4.50 | −0.75 | −4.93 |  | 0.07 | Within ±0.12 |
| −5.25 | −4.50 | −1.00 | −5.14 | −0.12 | −0.01 | |
| −5.50 | −4.50 | −1.25 | −5.36 | −0.12 | 0.02 | |
| −5.75 | −6.00 | 0.00 | −5.72 |  | 0.03 | |
| −6.00 | −6.00 | −0.25 | −5.93 | −0.12 | −0.05 | |
| −6.25 | −6.00 | −0.50 | −6.13 | −0.12 | 0.00 | Within ±0.18 |
| −6.50 | −6.00 | −1.00 | −6.54 |  | −0.04 | |
| −6.75 | −6.00 | −1.25 | −6.75 |  | 0.00 | |
| −7.00 | −6.00 | −1.25 | −6.75 | −0.12 | 0.13 | |
| −7.25 | −7.50 | 0.00 | −7.15 | −0.12 | −0.02 | |
| −7.50 | −7.50 | −0.50 | −7.55 |  | −0.05 | |
| −7.75 | −7.50 | −0.75 | −7.75 |  | 0.00 | |
| −8.00 | −7.50 | −1.00 | −7.94 |  | 0.06 | |
| −8.25 | −7.50 | −1.25 | −8.14 | −0.12 | −0.01 | |

FIG. 10

OPTOMETRIC APPARATUS

BACKGROUND OF THE INVENTION

1. Field of the Invention

The present invention relates to an optometric apparatus for examining (measuring) refractive power of an eye of an examinee subjectively.

2. Description of Related Art

There is known an optometric apparatus in which optical elements such as a spherical lens and a cylindrical lens are arranged in a test window provided in front of an eye of an examinee, and a forward-presented optotype is shown via the arranged optical elements for subjectively examining (measuring) the eye. And such apparatus is proposed that a plurality of spherical lenses with different power are arranged in three disks for spherical lenses, and the disks are rotated respectively to change a combination of the spherical lenses which are to be arranged in the test window so that spherical power (spherical refractive power) is applied to the eye. Also, proposed is an apparatus such that a plurality of cylindrical lenses with different power are arranged in two disks for cylindrical lenses (arranged in further positions than (posterior to) the disks for spherical lenses from the eye), and the disks are rotated respectively to change a combination of the cylindrical lenses which are to be arranged in the test window so that cylindrical power (cylindrical refractive power) is applied to the eye. And, a lens diameter of the optical elements used for such apparatus is about Φ20 mm (i.e. an effective diameter is about Φ19 mm)

Incidentally, when the spherical power and the cylindrical power, which are generated by combining a plurality of the spherical lenses and the cylindrical lenses, are applied to the eye, a difference between examination power, which is the simple sum of the power of the respective combined lenses, and resultant power through conversion for a spectacles wearing reference position needs to fall within a predetermined permissible difference. However, even though a difference between lens power and power through conversion for the spectacles wearing reference position is arranged to fall within the respective permissible difference in respect to each of the plurality of the lenses (single lens), when they are combined, the difference between the examination power and the resultant power through conversion for the spectacles wearing reference position becomes large. For example, in the case of a configuration in which a plurality of the spherical lenses with different power are arranged in the three (or more) disks for spherical lenses, the spherical lens with middle power (for example, power with an absolute value of 3D or more) is arranged also in the disk which is secondly closer to the eye. Therefore, when the disks for cylindrical lenses are arranged posterior to the three disks for spherical lenses (with respect to the eye), a difference between examination cylindrical power and resultant cylindrical power through conversion for a spectacles wearing reference position becomes large and does not fall within the permissible difference under the influence of refractive power of the spherical lenses arranged secondly and thirdly closer to the eye. Under such circumstances, an examination of high precision may not be performed.

SUMMARY OF THE INVENTION

The present invention has been made in view of the above circumstances and an object to overcome the above problems and to provide an optometric apparatus capable of performing an examination of high precision.

To achieve the objects and in accordance with the purpose of the present invention, an optometric apparatus for examining refractive power of an eye of an examinee subjectively, the optometric apparatus is provided with a test window through which the examinee looks at a presented optotype, a first spherical-power applying unit, including at least three disks for spherical lenses in which a plurality of spherical lenses with different power are respectively arranged, which applies spherical power to the eye by rotating the disks respectively to change a combination of the spherical lenses which are to be arranged in the test window, a cylindrical-power applying unit, including two cylindrical lenses having power of equal absolute values with opposite signs, which applies cylindrical power to the eye by changing a relative angle of a cylindrical axis of the respective cylindrical lenses which are to be arranged in the test window, a second spherical-power applying unit, including a spherical lens for correction with weaker power than step-change power of the spherical power applied by the first spherical-power applying unit, which applies spherical power to the eye by arranging the spherical lens for correction in the test window, an instruction unit which instructs examination spherical power and examination cylindrical power, a power-determining unit which determines power applied by the respective power-applying units so that a difference between the instructed examination spherical power and examination cylindrical power, and resultant spherical power and resultant cylindrical power through conversion for a spectacles wearing reference position falls within a predetermined permissible difference, and a control unit which controls driving of the respective power-applying units based on information about the determined power.

In another aspect of the present invention, an optometric apparatus for examining refractive power of an eye of an examinee subjectively, the optometric apparatus is provided with a test window through which the examinee looks at a presented optotype, a spherical-power applying unit, including at least three disks for spherical lenses in which a plurality of spherical lenses with different power are respectively arranged, which applies spherical power to the eye by rotating the disks respectively to change a combination of the spherical lenses which are to be arranged in the test window, a first cylindrical-power applying unit, including at least two disks for cylindrical lenses in which a plurality of cylindrical lenses with different power are respectively arranged, which applies cylindrical power to the eye by rotating the disks respectively to change a combination of the cylindrical lenses which are to be arranged in the test window, a second cylindrical-power applying unit, including a cylindrical lens for correction with weaker power than step-change power of the cylindrical power applied by the first cylindrical-power applying unit, which applies cylindrical power to the eye by arranging the cylindrical lens for correction in the test window, an instruction unit which instructs examination spherical power and examination cylindrical power, a power-determining unit which determines power applied by the respective power-applying units so that a difference between the instructed examination spherical power and examination cylindrical power, and resultant spherical power and resultant cylindrical power through conversion for a spectacles wearing reference position falls within a predetermined permissible difference, and a control unit which controls driving of the respective power-applying units based on information about the determined power.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
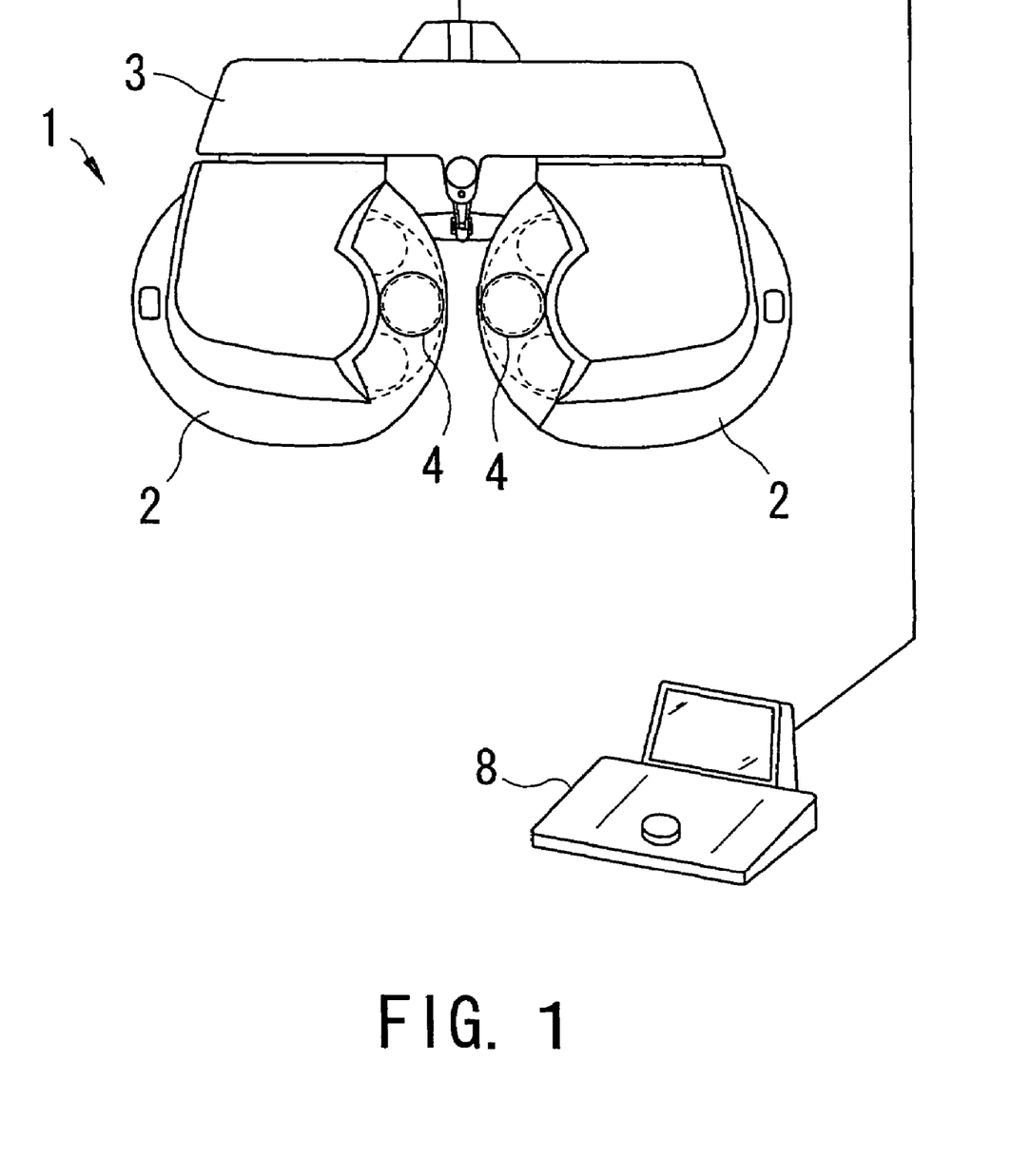
FIG. 1 is a front view showing an appearance of a subjective optometric apparatus consistent with the preferred embodiments when viewed from the examiner's side.

A detailed description of one preferred embodiment of an optometric apparatus consistent with the present invention will now given referring to the accompanying drawings. FIG. 1 is a front view showing an appearance of a subjective optometric apparatus consistent with the preferred embodiments when viewed from the examiner's side. A main body 1 of the optometric apparatus includes a pair of symmetric lens chamber units 2 and a moving unit 3 which suspends and supports (holds) these right and left lens chamber units 2 and has a sliding mechanism for adjusting an interval between the both units 2, and a convergence mechanism for adjusting a convergence angle (an intorsion angle) between the both units 2. The right and left lens chamber units 2 are provided with a test window 4 where after-mentioned optical elements such as a lens are to be arranged. A controller 8 inputs an operation signal into the main body 1.

Figure 2:
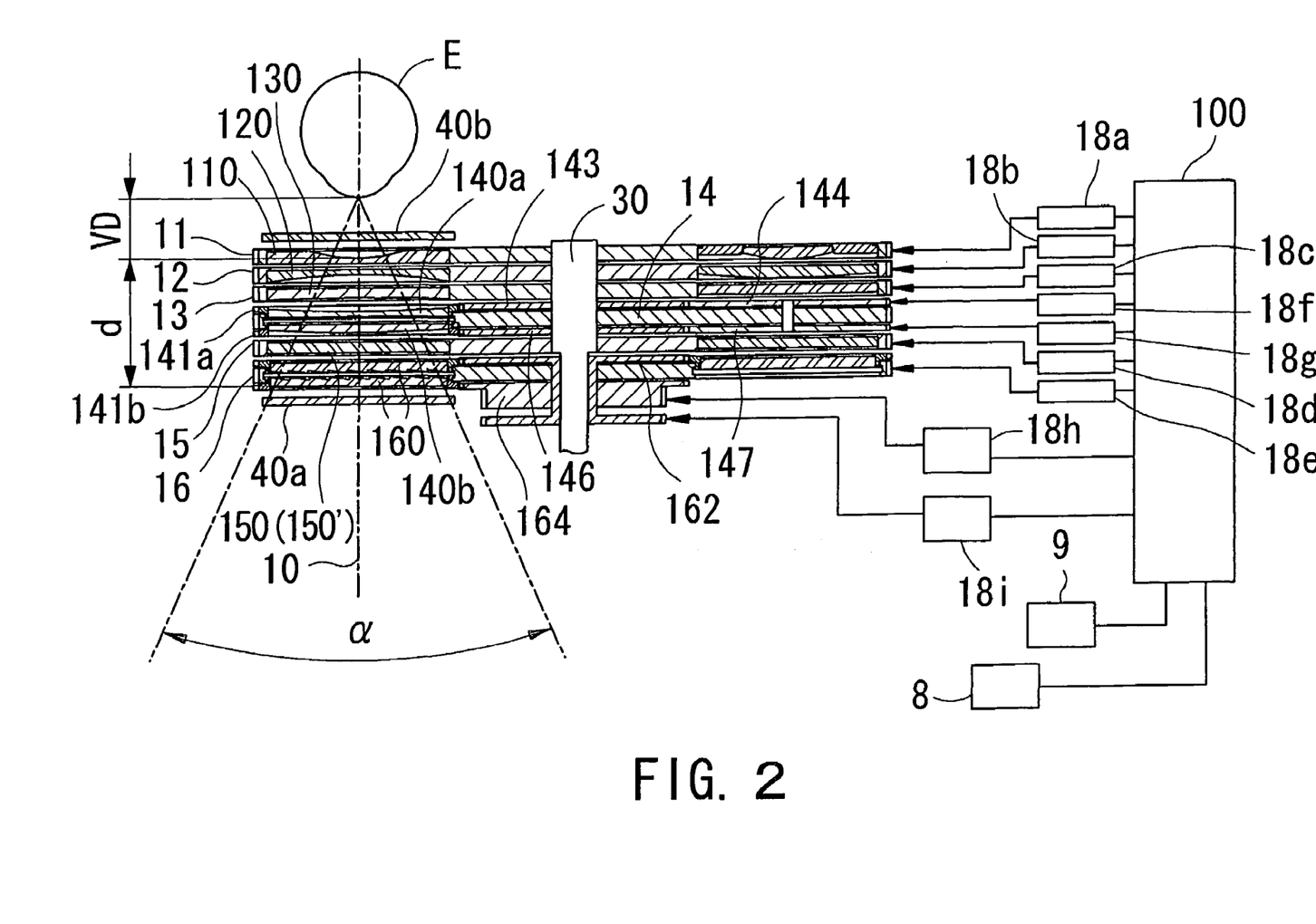
FIG. 2 is a view illustrating optical elements and their switching mechanism.

FIG. 2 is a view describing the optical elements arranged in the lens chamber unit 2 for a left eye, and a mechanism for switching the optical elements. Reference numeral 10 is an examination optical axis, and E presents the left eye of the examinee. In a housing of the lens chamber unit 2, arranged sequentially from the eye E are a disk 11 for strong spherical lenses, a disk 12 for middle spherical lenses, a disk 13 for weak spherical lenses, a frame 14 for cylindrical lenses, a disk 15 for auxiliary lenses, and a disk 16 for auxiliary lenses. The disks 11, 12, 13, 15 and 16 are arranged to be rotatable about a shaft 30 as its center. Gears are formed on outer circumferences of the respective disks, which are rotated by motors 18a-18e via unillustrated gears respectively, so that the optical elements arranged on the optical axis 10 may be switched. A protective glass 40a is arranged at the examiner's side of the test window 4, and a protective glass 40b is arranged at the eye E's side of the test window 4.

The disks 11, 12, 13, 15 and 16 respectively have five to eight holding holes for holding the optical elements. In this embodiment, the disks have the six holding holes each, one of which is a plain opening (a lens with 0D may be arranged therein).

Figure 3:
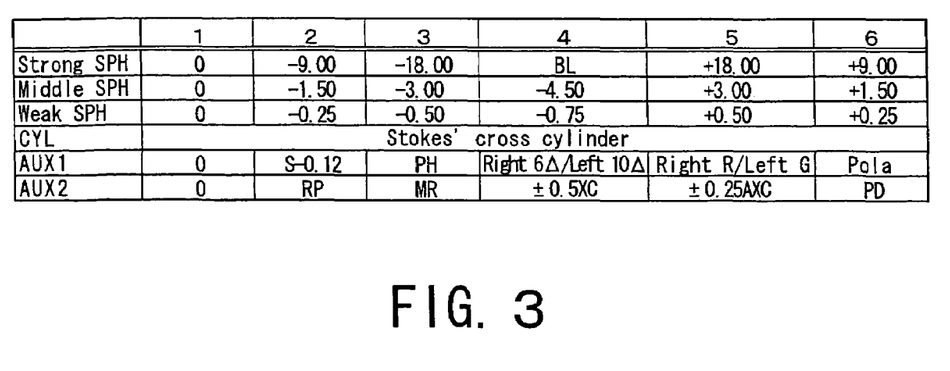
FIG. 3 shows an example of configuration of the optical elements arranged in respective disks.

Next, an example of configuration of the optical elements arranged in the respective disks and frame is shown in FIG. 3. Besides, D means diopter. And 0 presented in the figure is the plain opening (or the lens with 0D). In the disk 11 for strong spherical lenses, four spherical lenses 110 with strong power of −9D, −18D, +18D and +9D, and a cover plate (BL) are arranged. In the disk 12 for middle spherical lenses, five spherical lenses 120 with middle power of −1.5D, −3D, −4.5D, +3D and +1.5D, are arranged. In the disk 13 for weak spherical lenses, five spherical lenses 130 with weak power of −0.25D, −0.5D, −0.75D, +0.5D and +0.25D, are arranged. By combining the spherical lenses in the respective disks which are to be arranged in the test window 4, it is possible to apply spherical power ranging from −23.25D to +21.5D, at a change-step of ±0.25D, to the eye E.

In the disk 15 for auxiliary lenses, arranged are five auxiliary lenses 150: a spherical lens 150' with power of −0.12D for spherical power correction; a pinhole (PH); a dispersing prism (right6Δ/left10Δ); a green filter (G)(a red filter (R) for a right eye); and a polarizing plate (Pola). In the disk 16 for auxiliary lenses, arranged are five auxiliary lenses 160: a rotary prism (RP); a Maddox lens (MR); a cross-cylinder lens (XC) with power of ±0.5D; an auto cross-cylinder lens (AXC) with power of ±0.25D; and a plain lens (PD) provided with a mark for adjusting an eye width. Among them, the rotary prism and the auto cross-cylinder lens are arranged to be rotatable about the optical axis 10. The rotary prism which is closer to the eye E is mounted to be rotatable by a holder, and a gear thereof engages with a sun gear 162 which is rotatable about the shaft 30. The sun gear 162 is rotated by a motor 18i. The rotary prism which is further from the eye E is also mounted to be rotatable by a holder, and a gear thereof engages with a sun gear 164 which is rotatable about the shaft 30. The sun gear 164 is rotated by a motor 18h.

In the frame 14 for cylindrical lenses, two cylindrical lenses 140a and 140b having power of equal absolute values with opposite signs respectively, are arranged to be rotatable about the optical axis 10, respectively via disks 141a and 141b. These two cylindrical lenses 140a and 140b are arranged such that cylindrical power, which is generated by changing a relative angle E of respective cylindrical axes, may be consecutively changed and constitute a so-called Stokes' cross cylinder optical system. In this embodiment, the power of the cylindrical lens 140a is −3.625D, and that of the cylindrical lens 140b is +3.625D. The disk 141a holding the cylindrical lens 140a engages with a sun gear 143 which is rotatable about the shaft 30, and a gear 144 coupled to the sun gear 143 is rotated by a motor 18f. In the same manner, the disk 141b holding the cylindrical lens 140b engages with a sun gear 146 which is rotatable about the shaft 30, and a gear 147 coupled to the sun gear 146 is rotated by a motor 18g.

The above-described optical elements arranged in the respective disks and frame have a basically large diameter of Φ30 mm Φ40 mm (effective diameter of Φ29 mm-Φ39 mm). It is preferable that the optical elements have diameters of Φ36 mm (effective diameter of Φ35 mm) or more, which are used for a general framework examination. In this embodiment, the optical elements have the effective diameter of Φ35 mm. The eye E looks at an optotype arranged and presented ahead on the optical axis 10 via the optical element shaving the large diameter. By using the optical elements having the large diameter, it is possible to make a viewing angle α of the eye E larger than a conventional optical element having an effective diameter of Φ19 mm, so that intervention of adjustment caused by a peering-into effect (so-called instrument myopia) may be prevented. Further, the spherical lenses are arranged in the three disks effectively, so that the apparatus may be prevented from being upsized.

At the time of optometry, a distance VD between a cornea vertex of the eye E and a position of the spherical lens 110 (a spectacles wearing reference position) in the disk 11 which is the closest to the eye E is set as a predetermined distance (in Japan, VD is generally 12 mm) Since the effective diameter of the optical elements (the auxiliary lens 160) in the disk 16 which is the furthest from the eye E, and a lens distance d determine the viewing angle α of the eye E, they are arranged to have the viewing angle α of 40° or more, or preferably 45° or more. For example, assuming that the effective diameter of the optical element is Φ35 mm and the lens distance d is 28 mm, the viewing angle α becomes 46°. Besides, a diameter of the protective glass 40a which is arranged in the test window 4 is made larger than the optical elements to secure the above-mentioned viewing angle α.

However, for the strong-power spherical lens, its thickness increases as its lens diameter is enlarged. In order to deal with the problem, as for the spherical lenses with negative power, an optical zone having refractive power is secured in a range of at least the viewing angle α, and its peripheral side is cut flatly or its edges are widely chamfered. On the other hand, as for the spherical lenses with positive power, the optical zone having the refractive power is secured in the range of at least the viewing angle α, and a part of the holding hole of the disk 11, which is not covered by the lens, is complemented by a transparent member or the like. Besides, the cylindrical lenses may have the same constitution. Further, as for the rotary prism, its thickness may be reduced if a Fresnel prism, in which step-like angles of refraction are formed, is adopted.

Figure 4:
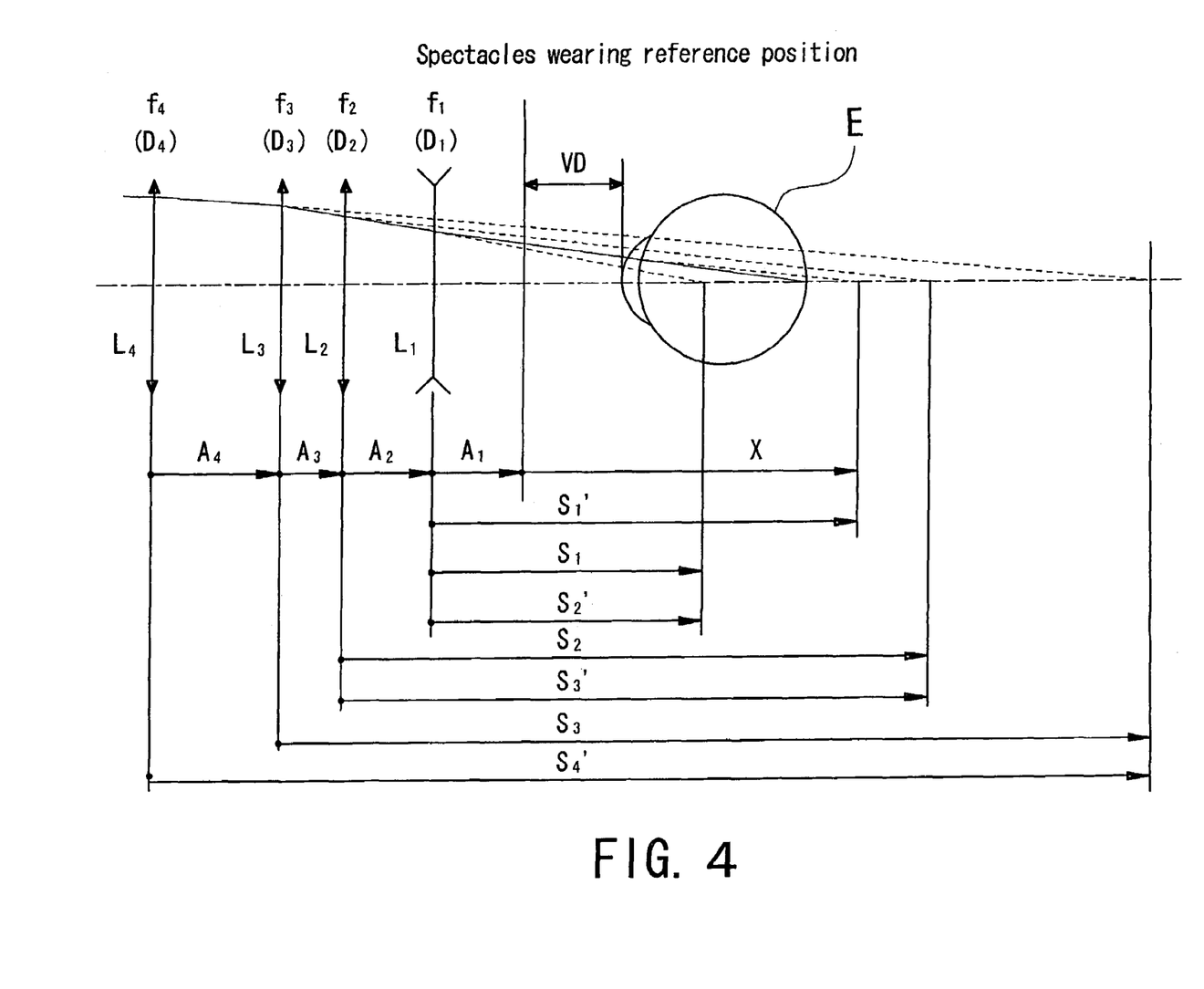
FIG. 4 is a view showing a relation of image formation when a plurality of lenses are combined.

Here will be described a difference between examination power and resultant power through conversion for a spectacles wearing reference position when a plurality of the lenses are combined. FIG. 4 is a view showing a relation of image formation when a plurality of the lenses are combined. Besides, in FIG. 4, four lenses as L1, L2, L3 and L4 are arranged sequentially from the vicinity of the eye E. Further, a paraxial formula for a thin walled lens is utilized here. The following Conditional Expressions 1 and 2 hold for the respective lenses.

$$\frac{1}{f_n} = \frac{1}{S'_n} - \frac{1}{S_n}$$ (Expression 1)

$$S_n = S_{n-1} + A_n$$ (Expression 2)

The above-mentioned Expressions 1 and 2 hold for every lens. If the lenses are four in number, n=4 is set. $f_n$ indicates a focal length of each lens, $S_n$ indicates an object distance of each lens, $S'_n$ indicates an image distance of each lens, and $A_n$ indicates a lens interval. Besides, it is assumed that S0=X, and A1 is a distance between a spectacles wearing reference position (a reference position, hereinafter) and the lens L1.

When power Dn through conversion for the reference position is obtained for each single lens, the focal length fn of each lens is obtained according to the following Expression 3.

$$f_n = \frac{1000}{D_n} + \sum_{i=1}^{n} A_i$$ (Expression 3)

Then, resultant power D0 through conversion for the reference position when the respective lenses are combined is obtained by the following Expression 4.

$$D_0 = \frac{1000}{X}$$ (Expression 4)

And then, the difference between the examination power and the resultant power through conversion for the reference position is further obtained.

Figure 5:
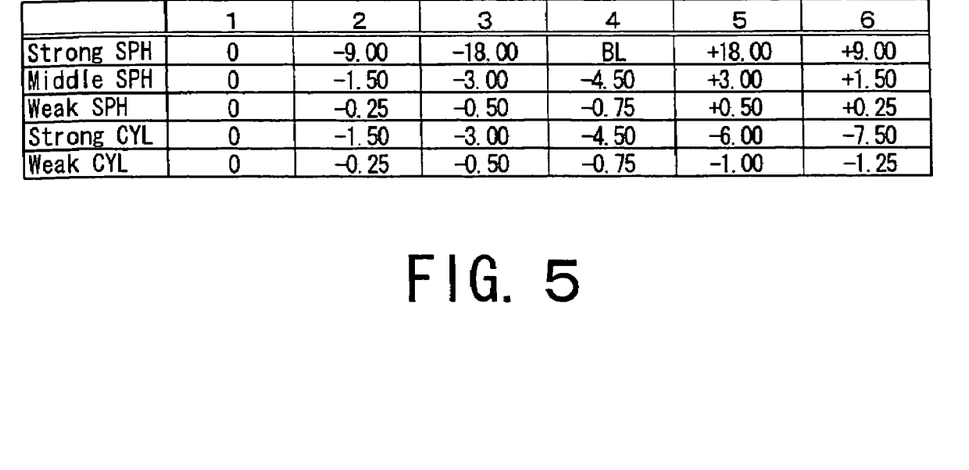
FIG. 5 shows an example of lens configuration in a combination of each spherical lens in three disks and each cylindrical lens in two disks.
Figure 6:
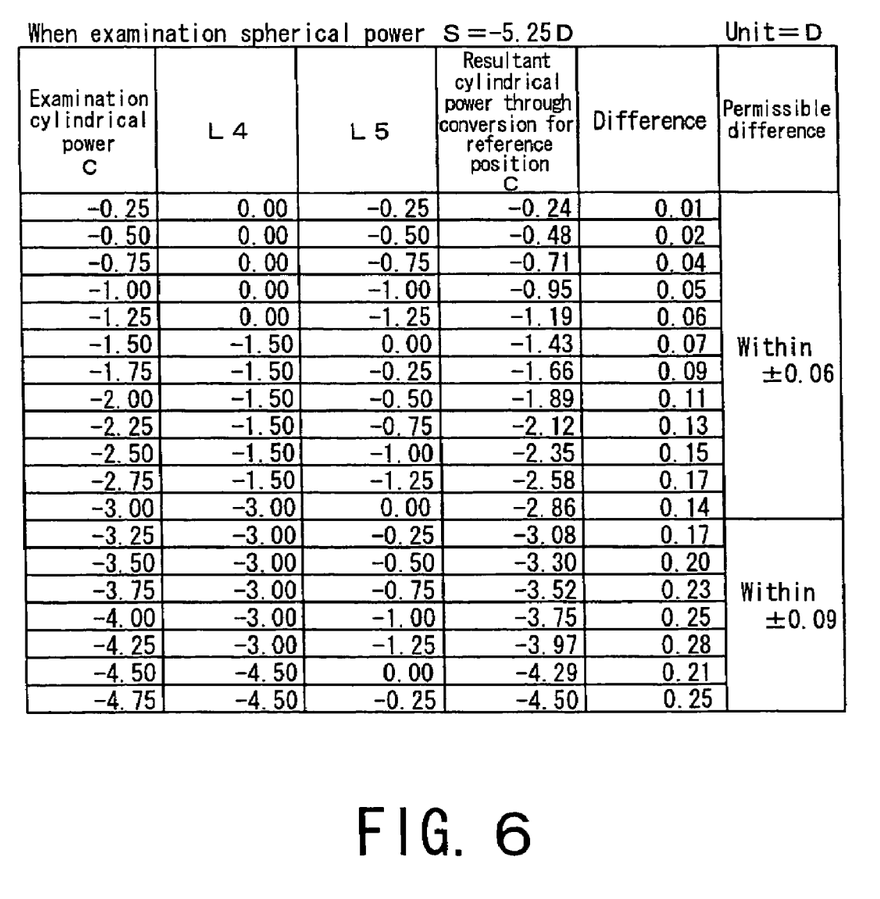
FIG. 6 shows examples of a difference between examination cylindrical power and resultant cylindrical power through conversion for a spectacles wearing reference position.
Figure 7A:
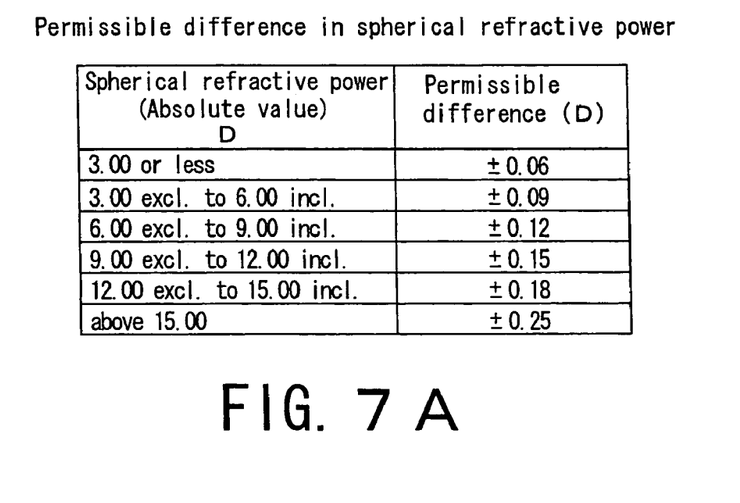
FIGS. 7A and 7B show examples of each permissible difference in spherical refractive power and cylindrical (astigmatic) refractive power.
Figure 7B:
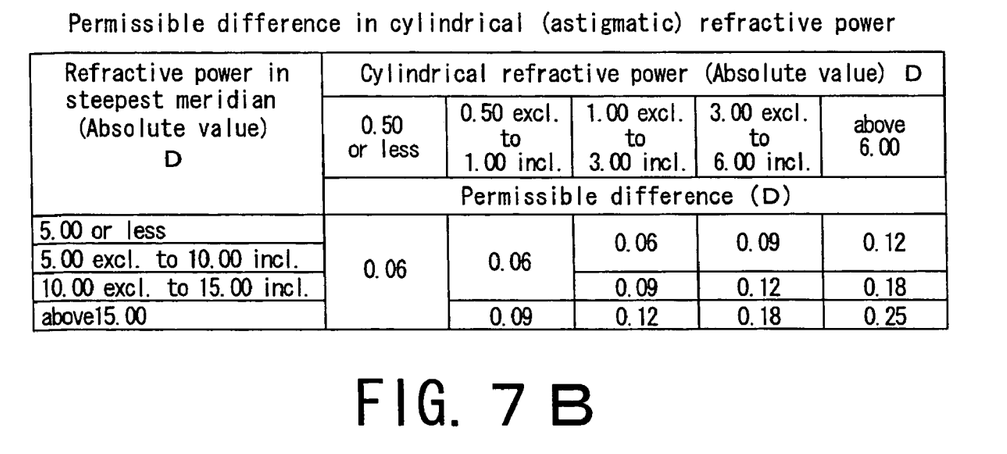

Here, the difference between the examination power and the resultant power through conversion for the reference position is obtained with regard to the combination of five lenses where the spherical lenses are arranged in three disks and the cylindrical lenses are arranged in two disks. A condition is made that the spherical lenses are respectively arranged in L1, L2 and L3, and the cylindrical lenses are respectively arranged in L4 and L5, and A1 is 0 mm and A2 to A5 are respectively 4 mm. The lens configuration is as shown in FIG. 5. In addition, in a case where the spherical lenses of 0D, −4.5D and −0.75D for example are arranged in L1, L2 and L3 respectively so that the examination power is the spherical power of −5.25D, the power of the cylindrical lenses arranged in L4 and L5 respectively is changed to obtain calculation results, and examples thereof are shown in FIG. 6. Assuming that each permissible difference in spherical refractive power and cylindrical (astigmatic) refractive power is as shown in FIGS. 7A and 7B, and that examination cylindrical power is simply the sum of the power of the cylindrical lenses arranged in L4 and L5, a difference between the examination cylindrical power and resultant cylindrical power through conversion for the reference position does not fall within a permissible difference in respect of all the lenses of which the examination cylindrical power is greater than −1.50D.

As a remedy for this, described will be a case where cylindrical lenses 140a and 140b (the Stokes' cross cylindrical optical system) is used to generate the cylindrical power. Assuming that the power of each of the cylindrical lenses 140a and 140b is Dc, a cylindrical angle difference therebetween is ε, generated cylindrical power is Dε, and a generated cylindrical axial angle is Ax, the following Relational Expressions 5 and 6 hold.

$$D\epsilon = -2Dc \cdot \sin\epsilon$$ (Expression 5)

$$Ax = (\epsilon/2) - 90°$$ (Expression 6)

In addition, in the cylindrical lenses 140a and 140b (the Stokes' cross cylindrical optical system), spherical power is developed concurrent with the generation of the cylindrical power. The developed spherical power Ds is obtained by the following Expression 7.

$$Ds = -D\epsilon/2$$ (Expression 7)

As mentioned above, in the cylindrical lenses 140a and 140b (the Stokes' cross cylindrical optical system), the cylindrical angle difference ε is changed within a range of 2Dc to generate the cylindrical power Dε. Thus, the difference between the examination cylindrical power when combined with the spherical lenses and the resultant cylindrical power through conversion for the reference position may be reduced to fall within the permissible difference.

Incidentally, the spherical power Ds which is developed concurrent with the generation of the cylindrical power Dε by the cylindrical lenses 140a and 140b (the Stokes' cross cylindrical optical system) requires correction. In this correction, another spherical lens with weaker power than power of the change-step of the spherical power is combined. In this embodiment, the power of the change-step of the spherical power is set to be ±0.25D, and a minimum value of a permissible difference in the spherical power is set to be ±0.06D (i.e. a range of the permissible difference is 0.12D). Accordingly, if the respective spherical lenses in the disks 11, 12 and 13 are combined with the spherical lens 150' for correction of −0.12D in the disk 15, the spherical power which is developed concurrent with the generation of the cylindrical power may be corrected, and the difference between examination spherical power and resultant spherical power through conversion for the reference position may fall within the permissible difference even if the spherical lens (the spherical lens 150') is further added.

Incidentally, as for the spherical lens 150' for correction, a spherical lens of −0.12D (or +0.12D, or of −0.13D or +0.13D) is used. Additionally, two spherical lenses of −0.06D and +0.06D may be used, and two spherical lenses of −0.08D and −0.04D (or those lenses with inverse signs) or the like may also be utilized. The power of the spherical lens 150' for correction may be determined based on the power of the change-step of the spherical power and the permissible difference, and is sufficiently obtained by subtracting the minimum range of the permissible difference (±0.06×2 in this embodiment) from the power of the change-step of the spherical power (±0.25D in this embodiment)

Figures 8A, 8B:
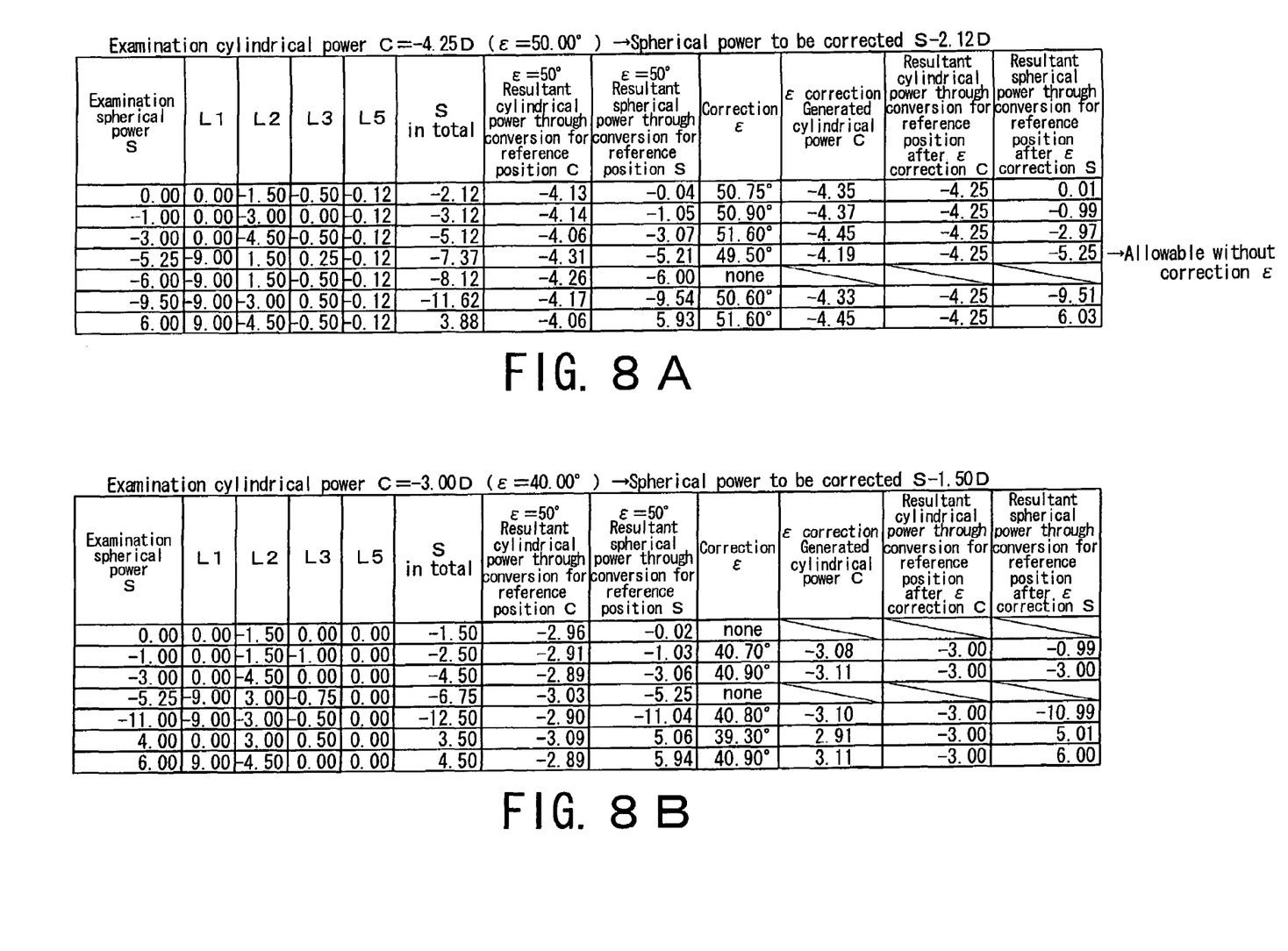
FIGS. 8A and 8B show examples of a combination of spherical lenses, cylindrical lenses as the Stokes' cross cylindrical optical system, and a spherical lens for correction.

FIGS. 8A and 8B show examples of the combination of the spherical lenses, the cylindrical lenses 140a and 140b (the Stokes' cross cylindrical optical system), and the spherical lens 150' for correction. In this case, it is assumed that the spherical lenses with the lens configuration as shown in FIG. 3 (in FIG. 5 likewise) are arranged in L1, L2 and L3, the Stokes' cross cylindrical optical system is arranged in L4 (i.e. the cylindrical lenses 140a and 140b form one unit), and the spherical lens 150' for correction of −0.12D is arranged in L5. Further, it is assumed that A1 is 0 mm, and A2 to A5 are respectively 4 mm.

FIG. 8A shows examples where the examination cylindrical power is −4.25D, and the examination spherical power is changed. While the cylindrical angle difference ε is 50 when the resultant cylindrical power through conversion for the reference position of −4.25D is generated while regarding the Stokes' cross cylindrical optical system as one unit, a great difference arises between the examination cylindrical power and the resultant cylindrical power through conversion for the reference position due to the power of the spherical lenses arranged in L1, L2 and L3. Further, when correction is made by an amount of the spherical power developed by the Stokes' cross cylindrical optical system, the resultant cylindrical power and the resultant spherical power through conversion for the reference position are changed. The great difference between the examination cylindrical power and the resultant cylindrical power through conversion for the reference position arises mainly because, when the disks other than the closest of the three disks for spherical lenses to the eye E have relatively strong spherical power (the absolute value when combined is at least 3D or more), the correction is affected by the refractive power.

For example, if the examination spherical power is 0D, the spherical lenses of 0D, −1.50D, −0.50D and −0.12D are arranged in L1, L2, L3 and L5 respectively so as to correct the spherical power by −2.12D, which is approximately half of the examination cylindrical power of −4.25D. In this case, if the generated cylindrical power remains to be −4.25D (ε=500) while regarding the Stokes' cross cylindrical optical system as one unit, the resultant cylindrical power and the resultant spherical power through conversion for the reference position are −4.13D and −0.04D respectively, and the difference between the generated cylindrical power and the resultant cylindrical power through conversion for the reference position does not fall within the permissible difference. Thus, if the generated cylindrical power is changed to be −4.35D (ε=50.75°), the resultant cylindrical power and the resultant spherical power through conversion for the reference position are −4.25 and 0.01D respectively to fall within the permissible difference.

In a case where the examination spherical power is −1.00D, the spherical lenses of 0D, −3.00D, 0D and −0.12D are arranged in L1, L2, L3 and L5 respectively so as to correct the spherical power by −2.12D, resulting that the resultant cylindrical power and the resultant spherical power through conversion for the reference position are −4.14D and −1.05D respectively not to fall within the permissible difference if the generated cylindrical power remains to be −4.25D (ε=500). Thus, the generated cylindrical power is changed to be −4.37D ε=50.90°) to fall within the permissible difference.

In a case where the examination spherical power is −9.50D, the spherical lenses of −9.00D, −3.00D, +0.50D and −0.12D are arranged in L1, L2, L3 and L5 respectively so as to correct the spherical power by −2.12D, resulting that the resultant cylindrical power and the resultant spherical power through conversion for the reference position are −4.17D and −9.54D respectively not to fall within the permissible difference if the generated cylindrical power remains to be −4.25D (ε=50°). Thus, the generated cylindrical power is changed to be −4.33D (ε=50.60°) to fall within the permissible difference.

Incidentally, FIG. 8B shows examples where the examination cylindrical power is −3.00D, and the examination spherical power is changed.

At the time of the optometry, the examiner gives instructions on the examination spherical power and the examination cylindrical power by using the controller 8. A control part 100 arranges the optical elements in the test window 4 by controlling driving of the motors 18a to 18i based on an instruction signal of the examination power from the controller 8. If the instruction on the examination cylindrical power is not given (i.e. if only the instruction on the examination spherical power is given), the combination of the respective lenses is determined in order that the sum of the respective power of the spherical lenses 110, 120 and 130 (including the openings) comes to the instructed examination spherical power, and is switched to be arranged in the test window 4. If the instruction on the examination cylindrical power is given, based on the instructed examination spherical power and examination cylindrical power, the combination of the respective power of the respective lenses (the spherical lenses 110, 120 and 130, and the spherical lens 150' for correction (including the openings)) is determined as well as the cylindrical power (the cylindrical angle difference ε generated by the cylindrical lenses 140a and 140b in accordance with the spherical power is determined. And, these combinations are previously stored in a memory 9, so that the control part 100 calls up combination information based on the instruction signal from the controller 8 and arranges the respective lenses in the test window 4 by controlling the driving of the respective motors. Incidentally, instead of previously storing the combination information in the memory 9, the control part 100 may determine the combination through occasional calculation.

Figure 9:
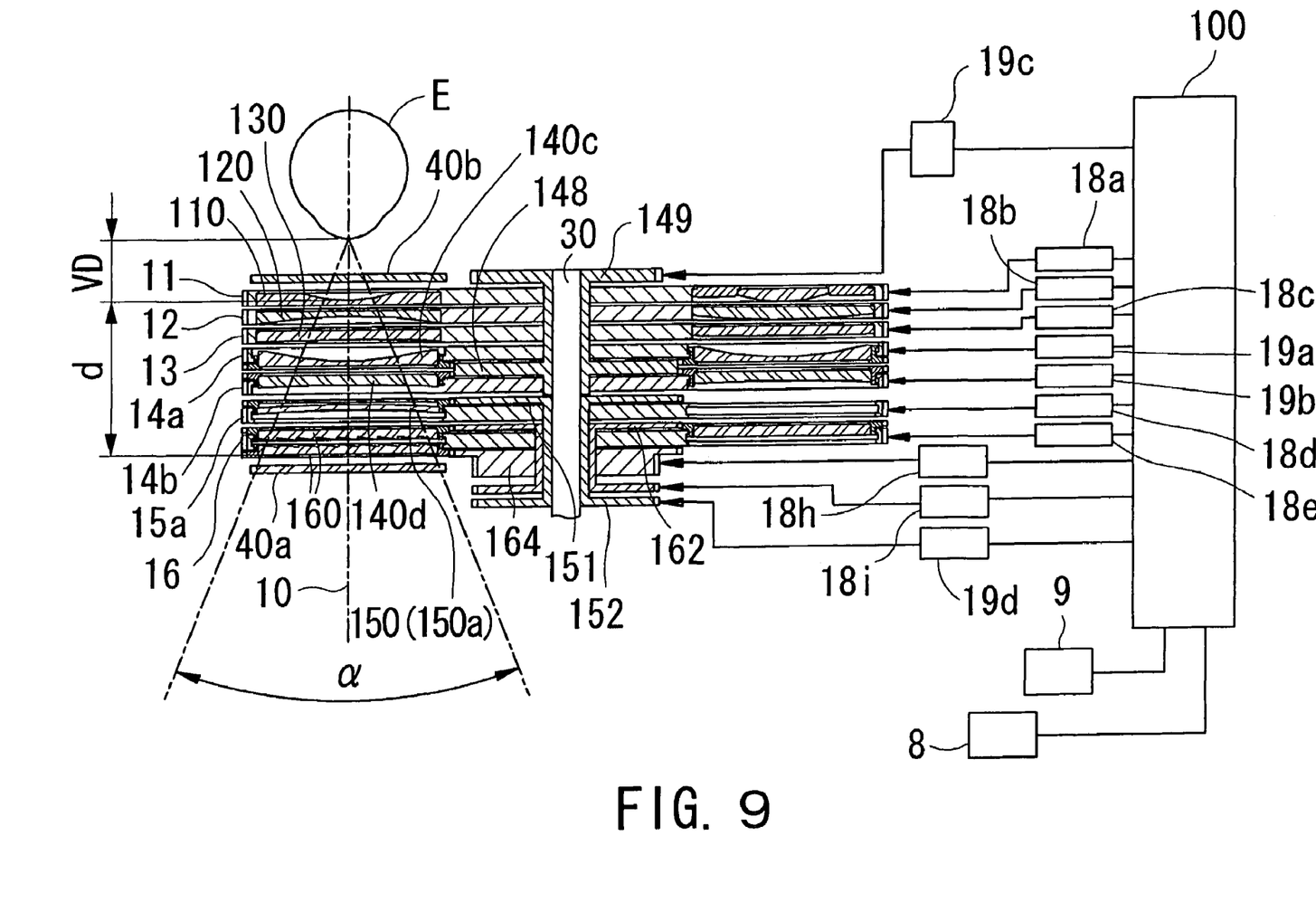
FIG. 9 is a view illustrating the optical elements and their switching mechanism consistent with the second preferred embodiment.

FIG. 9 is a view illustrating the optical elements and their switching mechanism in an apparatus consistent with the second preferred embodiment. The same components as in FIG. 2 are provided with the same reference numerals.

A disk 14a for strong cylindrical lenses has six holding holes, and five cylindrical lenses 140c with strong power of −1.5D, −3D, −4.5D, −6D and −7.5D are arranged in the five holding holes other than the opening. A disk 14b for weak cylindrical lenses has six holding holes, and five cylindrical lenses 140d with weak power of −0.25D, −0.5D, −1.75D, −1D and −1.25D are arranged in the five holding holes other than the opening. The disk 14a is rotated by a motor 19a and the disk 14b is rotated by a motor 19b. Further, the cylindrical lenses 140c and 140d are held by disks, which are respectively rotatable about the optical axis 10, and gears of these disks engage with a sun gear 148 being rotatable about the shaft 30, and a gear 149 coupled to the sun gear 148 is rotated by a motor 19, so that the cylindrical lenses 140c and 140d are rotated simultaneously about the optical axis 10 and cylindrical axes are changed.

Arranged in a disk 15a is an auxiliary lens 150 including a cylindrical lens 150a with power of −0.12D for cylindrical power correction. The cylindrical lens 150a for correction is held by a disk rotatable about the optical axis 10, and the disk engages with a sun gear 151. A gear 152 coupled to the sun gear 151 is rotated by a motor 19d, so that the cylindrical lens 150a for correction is rotated about the optical axis 10 and its cylindrical axis is changed.

As described above, when the disks 14a and 14b provided with a plurality of the cylindrical lenses with different power are rotated to switch and arrange the cylindrical lenses 140c and 140d in the test window 4 for applying the examination cylindrical power instructed by the controller 8 to the eye E, the difference between the examination cylindrical power and the resultant cylindrical power through conversion for the reference position does not fall within the permissible difference.

As a remedy for this, in the apparatus of the second preferred embodiment, the cylindrical lens 150a for correction is used, and the combination of the cylindrical lenses is determined according to the spherical power so that the difference between the examination cylindrical power and the resultant cylindrical power through conversion for the reference position falls within the permissible difference.

Figure 10:
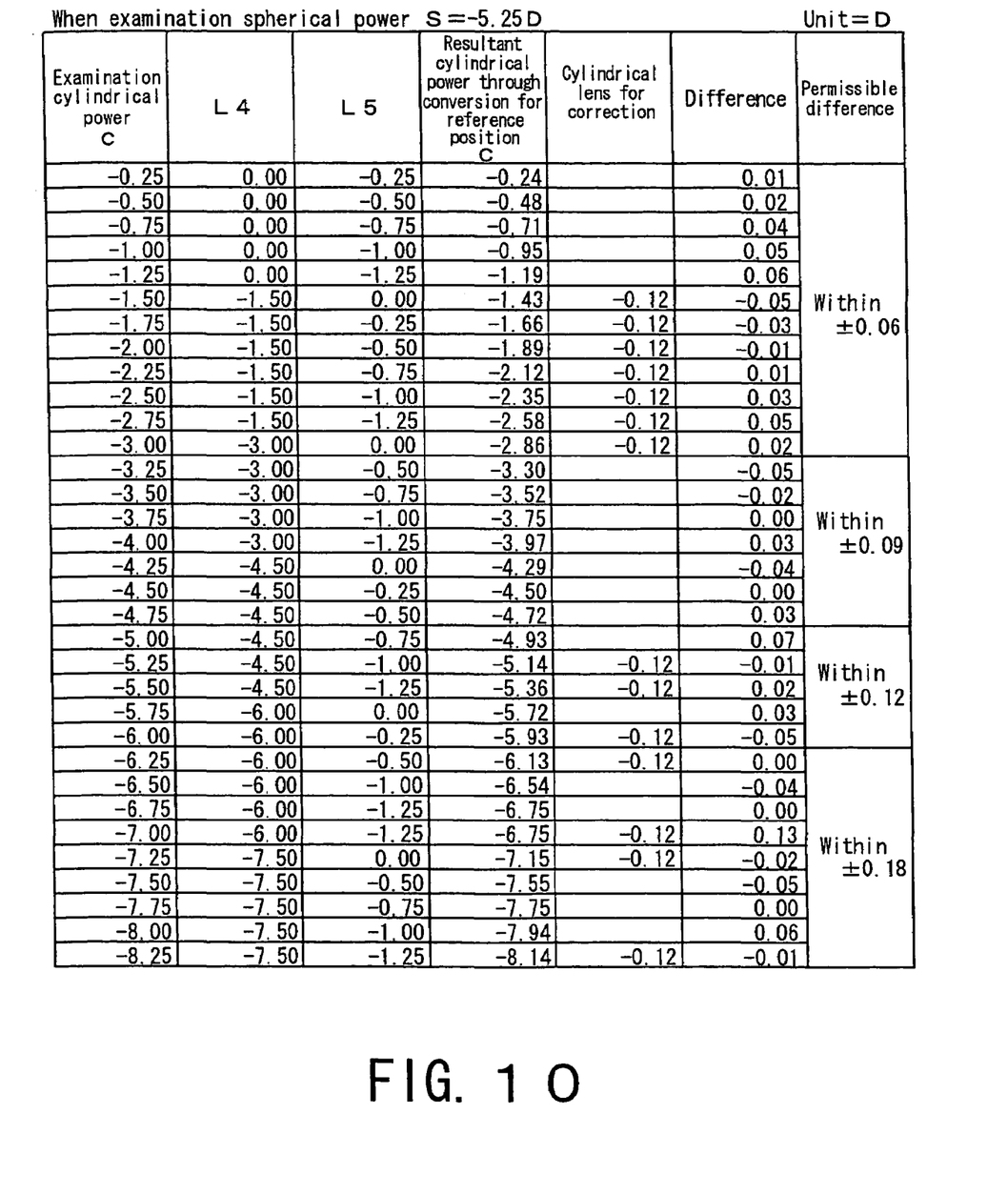
FIG. 10 shows examples of a combination of the cylindrical lenses and the cylindrical lens for correction.

FIG. 10 shows examples of the combination. Besides, in calculating the power through conversion for the reference position, it is assumed that the number of the lenses is set as n=5 in Expressions 1 to 4 mentioned above, and the spherical lenses are arranged in L1, L2 and L3 as well as the cylindrical lenses are arranged in L4 and L5. The distances A2 to A5 between the lenses are respectively 4 mm. In addition, in the combination with the cylindrical lens 150a for correction, as the refractive power is weak, the influence of the conversion for the reference position may be ignored.

For example, when the examination spherical power instructed by the controller 8 is −5.25D, the combination of the spherical lenses remains to be the same. However, for the combination of the cylindrical lenses arranged in L4 and L5, the cylindrical lenses are selected such that the difference between the examination cylindrical power and the resultant cylindrical power through conversion for the reference position falls within the permissible difference. If the combination of the cylindrical lenses arranged in L4 and L5 only does not make that difference fall within the permissible difference, the cylindrical lens 150a for correction is combined.

By previously storing the combination in the memory 9, the control part 100 calls up the combination information from the memory 9 based on the instruction signal from the controller 8, and arranges the respective lenses in the test window 4 by controlling the driving of the respective motors. Incidentally, if the power of the cylindrical lens for correction of −0.12D only is insufficient for the correction, the insufficiency may be accommodated by adding another cylindrical lens for correction of −0.25D to the disk 15a for auxiliary lenses. As the power of the cylindrical lens for correction is determined based on the power of the change-step of the cylindrical power and the permissible difference, the cylindrical lens with weaker power than at least the power of the change-step of the cylindrical power is prepared. In addition, a plurality of the cylindrical lenses for correction with different power may be prepared and selectively used. The method of combining the cylindrical lenses for correction in the second preferred embodiments is applicable to the case of using the Stokes' cylindrical optical system.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optometric apparatus for examining refractive power of an eye of an examinee subjectively, the optometric apparatus comprising:

a test window through which the examinee looks at a presented optotype;

a spherical-power applying unit, including at least three disks for spherical lenses in which a plurality of spherical lenses with different power are respectively arranged, which applies spherical power to the eye by rotating the disks respectively by a motor to change a combination of the spherical lenses to be arranged in the test window;

a first cylindrical-power applying unit, including
two cylindrical lenses having power of equal absolute values with opposite signs, which applies cylindrical power to the eye by rotating the cylindrical lenses respectively by a motor and changing a relative angle of a cylindrical axis of the respective cylindrical lenses to be arranged in the test window, or
at least two disks in which a plurality of cylindrical lenses with different power are respectively arranged, which applies cylindrical power to the eye by rotating the disks respectively by a motor and changing a combination of the cylindrical lenses to be arranged in the test window;

a second cylindrical-power applying unit, including a disk in which a cylindrical lens for correction with weaker power than step-change power of the cylindrical power applied by the first cylindrical-power applying unit is arranged, which applies cylindrical power to the eye by rotating the disk by a motor and arranging the cylindrical lens for correction in the test window;

a control unit which outputs an instruction signal for instructing examination spherical power and examination cylindrical power;

a memory which stores:

combinations of the spherical lenses to be arranged in the test window, which are determined so that the sum of the power of the spherical lenses to be arranged in the test window is equal to the examination spherical power instructed by the control unit; and combinations of the cylindrical lenses to be arranged in the test window, which are determined so that a difference between the examination cylindrical power instructed by the control unit and resultant cylindrical power through conversion for a spectacles wearing reference position of the cylindrical lenses to be arranged in the test window by the first cylindrical-power applying unit falls within a permissible difference, where the combinations such that the difference between the examination cylindrical power and the resultant cylindrical power does not fall within the permissible difference are further combined with the cylindrical lens for correction of the second cylindrical-power applying unit; and a control unit which calls up combination information from the memory based on the instruction signal from the control unit, and controls driving of the motors of the respective power-applying units based on the called-up combination information.

2. The optometric apparatus according to claim 1, wherein an effective diameter of the respective spherical lenses and cylindrical lenses is not less than Φ29 mm.

* * * * *